A. Hays,
Surgical Splint.
No. 232. Reissued Mar. 8, 1853.
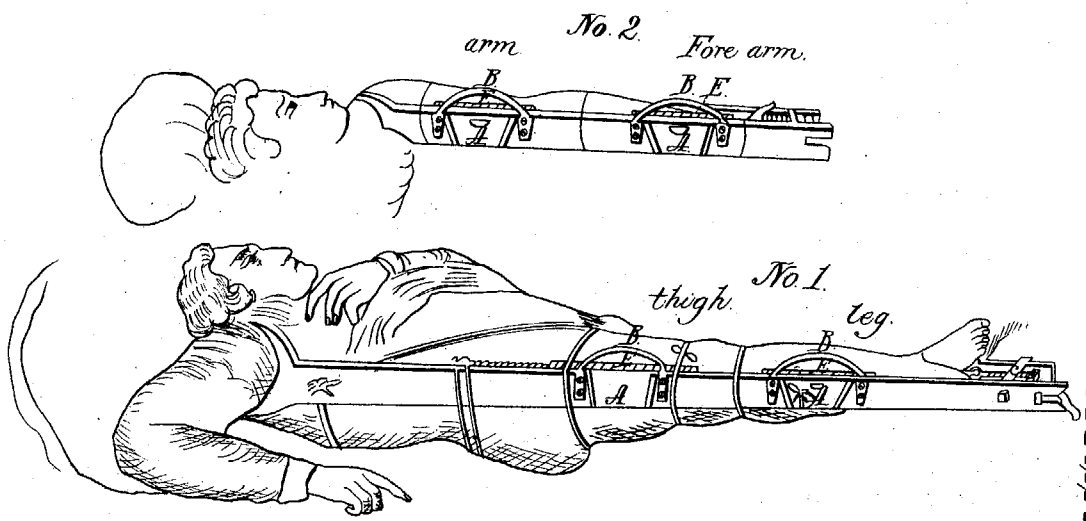
Inventor:
Adam Hays.
AM. PHOTO-LITHO. CO. N.Y. (OSBORNE'S PROCESS.)

UNITED STATES PATENT OFFICE.

ADAM HAYS, OF PITTSBURG, PENNSYLVANIA.

IMPROVEMENT IN SPLINTS FOR FRACTURES.

Specification forming part of Letters Patent No. 7,561, dated August 13, 1850; Reissue No. 232, dated March 8, 1853.

*To all whom it may concern:*

Be it known that I, ADAM HAYS, formerly of the city of Madison, county of Jefferson and State of Indiana, now of the city of Pittsburg, State of Pennsylvania, have invented a new and improved construction of splints for treating simple or compound fractures or other injuries or diseases of the thigh, leg, arm, and forearm, or any other part of the system in which extension and counter-extension can be beneficially applied so as to keep the parts in their proper relative position, at the same time affording free access to dress the parts as often as necessary by means of the brace and slide, which will enable the surgeon to retain the injured or diseased part in its proper position, and which he verily believes has not been known or used prior to the invention thereof by your petitioner.

The nature of my invention is such as to enable the surgeon to keep up permanent extension and counter-extension throughout the treatment necessary, so as to keep the parts in their proper relative position, and at the same time afford opportunity for dressing as often as may be necessary without risking any displacement of the parts, and thus accomplish a most important object in the management of such cases.

To enable others skilled in the art and science of surgery to make and use my invention, I will proceed to describe its construction and operation.

I take the splint and dressing, such as has been in public use and known as "Physick's Improvement of Dassault" (see No. 1 in the drawings,) or, in case both limbs require the treatment, "Gibson's Improvement of Hagedorn," (see No. 2 in the drawing,) which is also in public use. Opposite the fracture, disease, or injury I cut out a portion of the splint (see letter A in the Drawings Nos. 1 and 2) large enough to give the surgeon free access to dress the parts as often as may be necessary. The slide is cut one-fourth or one-third of an inch larger on each side of its upper edge than the lower. The upper and lower portions of the splint thus separated I unite by a steel or iron brace, of an arched shape, (see letter B in the Drawings Nos. 1 and 2,) so as to hold the two portions of the splint in their proper places. The piece of the splint cut out, or a similar one, may be converted into a slide (see letter A, Nos. 1 and 2) to work in a groove on each end, (see letters C and D.) The slide can be drawn out at each dressing, the brace keeping the limb firmly in a proper position while dressing is accomplished. The extension and counter-extension being uniformly kept up, no displacement can take place. After each dressing the slide is to be returned to its proper place to give support to the parts. By means of the slip placed in the loops at the upper end of the lower splint and the lower end of the upper splint and the slide the whole is kept firm and fixed. The slip is marked letter C, and is shown with blue ink.

What I claim as my invention, and desire to secure by Letters Patent, is—

The cutting out a portion of the splint to afford an opportunity for dressing as often as may be necessary, the upper and lower portions of the splint being kept firmly united by means of the brace B, so as by extension and counter-extension to keep throughout the treatment the proper relative position of the parts concerned, the slide being replaced after each dressing, or any other device substantially the same.

ADAM HAYS.

Witnesses:
M. BUCKMASTER,
CH. MCCLURE HAYS.